United States Patent [19]
Bartish

[11] 4,102,921
[45] Jul. 25, 1978

[54] PRODUCTION OF CARBOXYLIC ACIDS AND ESTERS

[75] Inventor: Charles M. Bartish, Bethlehem, Pa.

[73] Assignee: Air Products & Chemicals, Inc., Allentown, Pa.

[21] Appl. No.: 791,121

[22] Filed: Apr. 26, 1977

[51] Int. Cl.$^2$ .................. C07C 51/10; C07C 51/12; C07C 67/36; C07C 67/37

[52] U.S. Cl. .................. 260/532; 260/410; 260/410.9 R; 260/413; 260/514 M; 260/515 R; 260/540; 260/541; 560/105; 560/114; 560/204; 560/232

[58] Field of Search .................. 260/488 K, 493, 496, 260/532, 413, 410, 410.9 R, 540, 514 M, 541, 468 M; 560/232, 114

[56] References Cited

U.S. PATENT DOCUMENTS

3,772,380  11/1973  Paulik et al. .................. 260/491

*Primary Examiner*—Vivian Garner
*Attorney, Agent, or Firm*—Russell L. Brewer; Barry Moyerman

[57] ABSTRACT

This invention relates to an improved process for the carbonylation of alcohols, esters, ethers and halide derivatives with carbon monoxide in the presence of a catalyst system comprising a Group VIII metal component and a halogen component. The improvement in the process resides in the use of a polydentate chelating phosphorus or arsenic ligand complexed with iridium as the Group VIII metal component.

12 Claims, No Drawings

PRODUCTION OF CARBOXYLIC ACIDS AND ESTERS

BACKGROUND OF THE INVENTION

1. Field of the Invention

This invention relates to carbonylation reactions of an alcohol, ether, ester, and halide derivative thereof with carbon monoxide to form carboxylic acids and esters.

2. Description of the Prior Art

Carbonylation processes for the preparation of carboxylic acids and esters from a variety of reactants are well known in the art. One of the better known carbonylation processes involves the synthesis of acetic acid by the reaction of methanol and carbon monoxide in the presence of a catalyst. Various catalyst systems have been reported as being effective for carbonylation processes, but each has had certain disadvantages, for example, instability of the catalyst, lack of product selectivity, low levels of catalyst reactivity, or loss of highly volatile catalyst from the reaction. Particular processes are shown in the following United States patents.

U.S. Pat. No. 3,530,168 shows a process for forming carboxylic acid esters by contacting an olefin, carbon monoxide and oxygen with a catalyst comprising a Group VIII noble metal, e.g. palladium complexed with a biphyllic phosphine or arsine ligand, i.e. those having an element with a pair of electrons capable of forming a coordinate bond with a metal atom and simultaneously having the ability to accept electrons from the metal of the catalyst.

U.S. Pat. Nos. 3,769,324 and 3,772,380 disclose processes for preparing aromatic and aliphatic carboxylic acids and esters by reacting an aromatic alcohol, ester, ether and halide derivative thereof with carbon monoxide in the presence of a catalyst consisting essentially of an iridium component and a halogen component. Monodentate phosphine and arsine ligands are the only ligands shown.

U.S. Pat. No. 3,887,595 discloses a process for carbonylating olefinic unsaturated hydrocarbons to form acids, esters and acid anhydrides by catalyzing the reaction with a zero valent palladium or platinum complex stabilized with a phosphine ligand.

U.S. Pat. No. 3,917,670 discloses a process for the carbonylation of organomercurials to form carboxylic acids. In that carbonylation process, a catalyst comprising palladium complexed with a phosphine ligand is employed.

U.S. Pat. No. 3,917,677 discloses a process for preparing carboxylic acid esters by reacting an ethylenically unsaturated compound, e.g. propylene, with carbon monoxide and an alcohol in the presence of a catalyst consisting essentially of a rhodium component and a tertiary organophosphorous compound free of halogen.

U.S. Pat. No. 3,852,346 discloses a process for preparing carboxylic acid anhydrides by reacting an olefin with carbon monoxide in the presence of a rhodium or iridium compound, an iodide component and regenerator.

U.S. Pat. No. 3,923,880 discloses a process for carbonylating alcohol and alcohol derivatives to form carboxylic acids using a catalyst complex containing cations of rhodium or iridium and an anionic moiety other than halide, e.g. tetraaryl borate, phosphate, sulphate, perchlorates, iodates and bromates.

SUMMARY OF THE INVENTION

This invention relates to an improved process for forming carboxylic acids and esters by the carbonylation of alcohols, esters, ethers and organo halides. The improvement constituting the basis of this invention resides in the employment of an iridium compound complexed with a polydentate phosphorus or arsenic chelating ligand as the catalyst and conducting the reaction at a temperature of from about 160° C to about 250° C.

The primary advantage of the catalyst component of this invention is that the catalyst component is much less volatile than the catalyst species formed when monodentate phosphorus and arsenic ligands are employed as promoters as was done previously in carbonylation reactions. Because the catalyst has lower volatility, it results in substantially reduced loss of catalyst. This factor is extremely important in view of the high cost of the catalyst component and the high concentration thereof required for producing commercial quantities of carboxylic acids and esters.

Another advantage of the invention is that the rate of carbonylation of alcohols and other reactants, although somewhat slower than the rate experienced with an iridium component stabilized with a monodentate phosphorus ligand, may be sufficiently fast for commercial production.

Another advantage of the catalyst is that they are readily soluble and thermally stable making them resistant to deposition of difficult to remove metal in process equipment.

DESCRIPTION OF THE PREFERRED EMBODIMENT

The important feature of this invention is the utilization of an iridium compound complexed or stabilized with a polydentate chelating phosphorus or arsenic ligand as a catalyst for alcohol carbonylation. The presence of the chelating phosphorus ligand, as opposed to a monodentate ligand, in the iridium compound reduces the volatility of the compound and thereby reduces the amount of catalyst that must be continually added to the process for synthesis of carboxylic acids and esters.

The chelating, polydentate phosphorus or arsenic ligands of this invention are of a type which, in the presence of carbon monoxide, have a greater binding between the iridium and phosphorus or arsenic atoms compared to the binding that is experienced between iridium complexed with monodentate phosphorus or arsenic atoms. Although not intending to be bound by theory, it is believed that it is because of this greater binding between the polydentate chelating phosphorus and arsenic ligands and iridium that the advantageous properties of the catalyst are achieved. The polydentate phosphorous ligands, in the presence of carbon monoxide, halide and the iridium compound, result in the formation of a catalyst shown as formula 1, and in the presence of alcohol reactant and acid media for example, a catalyst, as represented by formula 2, is formed. These catalyst species are as follows:

Formula 1   Formula 2

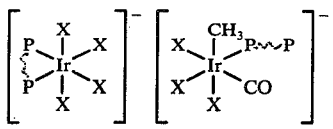

wherein in Formulas 1, 2, and 3 below, X is halogen.

On the other hand, as is generally known, the catalyst species which effects carbonylation of alcohols to form esters and acids, where monodentate phosphorus or arsenic ligands are employed, is represented by Formula 3. This complex forms readily as the monodentate phosphorus or arsenic ligands are displaced by CO or halide. This particular intermediate catalyst, in the presence of carbon monoxide, results in the formation of a highly volatile species, $Ir(CO)_3 X$ and $[Ir(CO)_2X]_2$, which thereby accounts for the losses of iridium metal from the reactor.

Formula 3

$$[Ir(CO)_2 X_2]^-$$

The catalyst component of this invention can be viewed as the reaction product of an iridium compound and a polydenate phosphine or arsine ligand of the formula:

$$R_1 R_2 P_1 A P_2 R_3 R_4$$

in which the ratio of ligand to iridium is at least about 1, and preferably 1–4
wherein:

$R_1$ and $R_3$ are alkenyl groups having from 2 to 6 carbon atoms, alkyl groups having from 1 to 6 carbon atoms, hydrogen atoms, aryl groups, and substituted derivatives thereof;

$R_2$ and $R_4$ are aryl groups and substituted aryl groups;

$P_1$ and $P_2$ are phosphorus and/or arsenic;

A is an arylene group, an alkenyl group having from 2 to 4 carbon atoms and substituted derivatives thereof; and $(CH_2)_n$ where $n$ is from 1–4.

The iridium complex with polydentate chelating phosphorus and arsenic ligands can be prepared in a variety of ways. In a typical reaction, solutions of dichlorodicarbonyliridium anion and the appropriate chelating diphosphine or arsine ligand are prepared in benzene. The solution of phosphine ligand is added to the dichlorodicarbonyl iridium anion solution and carbon monoxide evolves. After evolution of carbon monoxide ceases, an addition of sufficient diethyl ether is made to cause cloudiness. The solution then is cooled and a solid product recovered.

Examples of iridium compounds which can be used in forming the iridium-polydentate phosphine or arsine complex include iridium trichloride, iridium tribromide, iridium trichloridetrihydrate, iridium tetracarbonyl dichloride, iridium tetracarbonyl dibromide, iridium tris(-triphenylphosphine) iodide, iridium bis(triphenylphosphine) carbonyl chloride, iridium trinitrate, dimethylchloroiodo tris(triphenylphosphine) iridium, iridium oxide, and others commonly used in the art in forming the monodentate complexes.

It is understandable that some of the iridium-phosphine complexes, because of the differences in the ability of the ligands to bind the phosphorus or arsenic atom to the iridium atom, are more active in catalyzing the carbonylation reaction. Iridium catalysts having strong binding between ligand and metal, as would be expected where $R_1$, $R_2$, $R_3$ and $R_4$ are methyl groups, are highly inactive; whereas the iridium catalyst when $R_1$, $R_2$, $R_3$, and $R_4$ are phenyl, which results in weaker binding, has greater activity in catalyzing the reaction. By carefully weakening the binding, as for example by incorporating electron withdrawing groups, e.g. fluorine and nitro groups on a phenyl group, it is possible to weaken the binding even more and enhance activity. What must be avoided is the weakening of the binding to a degree such that carbon monoxide is able to replace both of the phosphorus atoms in the iridium complex. If that happens, then the intermediate catalyst as shown in formula 3 is formed.

The reaction rate is also affected by the group A in the formula as this also affects binding. For example, when A is $(CH_2)_n$ and $R_1$, $R_2$, $R_3$, and $R_4$ are phenyl, and $P_1$ and $P_2$ are phosphorus, $n$ must be 1, 2, 3 or 4 to produce an effective, non-volatile catalyst. After $n$ exceeds 4, the chelate effect, which stabilizes the non-volatile iridium complexes, diminishes rapidly. In other words, the binding becomes weaker. As a result, facile substitution of the phosphorus ligands on iridium by carbon monoxide occurs, leading to a volatile catalyst of the type shown in formula 3. It is somewhat surprising that where A is $(CH_2)_n$ and $n$ is equal to 1 or 3, faster reaction rates are observed, than where n is 2 or 4. For these reasons then, the methane or propane derivative is preferred.

The reactants which may undergo carbonylation in this process to form carboxylic acid and esters are selected from the class consisting of alcohols, having the formula ROH where R is a saturated hydrocarbyl radical having from 1 to 20 carbon atoms, alcohol derivatives, ethers, esters, said ethers and esters having the formula $R_a$—O—$R_a$ and

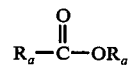

wherein $R_a$ is a saturated hydrocarbyl radical having from about 1 to 19 carbon atoms and wherein the total number of carbon atoms does not exceed about 20, and organo halides having the formula R—X where R is a saturated hydrocarbyl radical having from about 1 to 20 carbon atoms and X is a halogen atom selected from the group consisting of bromine, chlorine, and iodine. Examples of reactants from these classes include methanol, ethanol, propanol, isopropanol, butanol, hexanol, cyclohexanol, cyclopentanol, benzylalcohol, higher alcohols such as decanol, dodecanol, nonodecanol; ethers such as methyl ether, ethyl ether, isopropyl ether and butyl ether; acetates such as methyl acetate, ethyl acetate, pentyl acetate, methyl methacrylate, ethyl methacrylate, 2-ethylhexyl methacrylate; and organo halides such as methyl chloride, propyl bromide, heptyl iodide and the like.

As with prior art processes involving the carbonylation of alcohols, ethers, esters, and organohalides, the reaction is carried out by intimately contacting the reactant in either vapor or liquid phase with gaseous carbon monoxide in a liquid reaction medium, generally acidic, containing the iridium complex of a polydentate chelating phosphorus or arsenic ligand, and a halogen-containing promoting component. In addition, the temperature of the reaction is generally from about 160° C to 250° C with preferred temperatures being from about 190° C to 210° C. The pressure of carbon monoxide in the reaction generally is in the range of 1 to 15,000 psig, however, pressures of 5 to 1,000 psig are preferred. If the temperature falls below about 160° C, the reaction rate is extremely slow.

The concentration of iridium-polydentate phosphorus or arsenic ligand used in production of carboxylic acids is generally based on the moles of alcohol reactant employed. In a broad sense, the mole ratio of alcohol reactant to the mole ratio of iridium-phosphorus or arsenic ligand is from about 20 to about 26,000 with preferred proportions of from about 200 to 1,000. As might be expected from the theory advanced before, as the concentration of the iridium-polydentate phosphorus or arsenic complex is increased, the rate of reaction increases. However, concentrations of iridium metal above about 0.05 preferably about 0.01 moles per mole alcohol reactant do not result in significant operating advantages.

The halogen component used in the catalyst composition is a chlorine, iodine, or bromine providing compound. Its function is to act as a promoter and once an effective proportion of halogen providing component is provided in the reaction medium, the rate of reaction is not substantially influenced by additional quantities. Generally, the concentration of halogen providing component is adjusted to provide about 2 to 50,000 atoms halogen per atom of iridium and preferably from about 5 to 500 atoms halogen per atom of iridium. Examples of halogen providing compound include aryl halides, metal halides, ammonium halides, phosphonium halides, arsonium halides, stibonium halides and alkyl or hydrogen halides. Specific examples include methyl iodide, phenyl bromide, ethyl iodide, hydrogen iodide, and so forth.

The following examples are provided to illustrate preferred embodiments in the invention, and are not intended to restrict the scope thereof.

EXAMPLE 1

Di-[1,2-bis(diphenylphosphino)ethane]carbonyliridium(I)-chloride, (diphos)$_2$Ir(CO)Cl, was prepared by adding dropwise 5.14 mmoles of a solution of 1,2-bis(diphenylphosphino)ethane in 25 ml of benzene to 2.57 mmoles of Ir(PPh$_3$)$_2$(CO)(Cl) dissolved in 30 ml of benzene. A cream-yellow precipitate of the crystalline product formed. The crystals were filtered, washed with benzene, and dried in a vacuum. The compound was characterized as di-[1,2-bis(diphenylphosphino)ethane]carbonyliridium(I) chloride by its infrared spectrum and elemental analysis.

EXAMPLE 2

Acetic acid was prepared in these runs by mixing 5g methanol, 3.2g of 50% aqueous hydriodic acid, 52.5g acetic acid solvent in a vessel. The vessel was sealed and pressurized with carbon monoxide to an initial pressure of 750 psig. After a short induction period, methanol carbonylation began and was allowed to continue until the pressure had decreased to 350 psig. Varying amounts of iridium catalyst were added to provide a specific concentration of iridium metal on a mole per liter basis, and the amounts of ligand were varied. These and other operating conditions are also set forth in Table 1. The rate of acetic acid production is given in moles/liter/sec. The rate constant ($k$) is defined by the equation rate $= k[Ir][I]$ where Ir is the molar concentration of iridium metal and I is the concentration of iodine.

TABLE 1

| Run | Catalyst | Ligand | Ir Conc. × 10$^3$ mole/liter | P/Ir | Rate ×10$^4$, moles liter$^{-1}$ sec$^{-1}$ | k, L/M/sec | Temp.° C |
|---|---|---|---|---|---|---|---|
| 1 | Ir(H$_2$O)$_3$ Cl$_3$ (prior art) | | 1.57 | | 2.46 | 0.74 | 192° |
| 2 | Ir(H$_2$O)$_3$ Cl$_3$ (prior art) | | 4.06 | | 6.30 | 0.73 | 193° |
| 3 | Ir(CO)(P Ph$_3$)$_2$Cl (prior art) | triphenyl phosphine | 4.02 | 2 | 4.37 | 0.51 | 193° |
| 4 | Ir(CO)(P Ph$_3$)$_2$ Cl | dpm* | 8.07 | 1 | 2.02 | 0.12 | 194° |
| 5 | " | dpm | 8.07 | 1 | 2.95 | 0.17 | 192° |
| 6 | " | dpm | 8.07 | 1 | 3.19 | 0.18 | 193° |
| 7 | " | dpm | 8.07 | 2 | 1.05 | 0.06 | 193° |
| 8 | " | dpm | 8.07 | 4 | 0 | — | 193° |
| 9 | " | diphos** | 8.07 | 1 | 2.94 | 0.17 | 194° |
| 10 | " | diphos | 8.07 | 2 | 1.34 | 0.08 | 193° |
| 11 | " | diphos | 8.07 | 4 | 0.58 | 0.34 | 194° |
| 12 | " | diphos | 8.07 | 6 | 0.395 | 0.02 | 193° |
| 13 | " | dpp*** | 8.07 | 1 | 3.79 | 0.22 | 194° |
| 14 | " | dpp | 8.07 | 2 | 2.46 | 0.14 | 196° |
| 15 | " | dpp | 8.07 | 4 | 0.006 | 0.003 | 194° |
| 16 | " | dpb**** | 8.07 | 1 | 2.43 | 0.14 | 193° |
| 17 | " | dpb | 8.07 | 2 | 1.82 | 0.11 | 194° |
| 18 | " | dpb | 8.07 | 4 | 1.39 | 0.08 | 194° |
| 19 | " | dpb | 8.07 | 6 | 1.35 | 0.08 | 194° |

*bis(diphenyl phosphino) methane
bis(diphenyl phosphino) ethane *bis(diphenyl phosphino) propane ****bis(diphenyl phosphino) butane The results in the table show that the chelating-phosphine-ligand complexes of iridium are suitable catalysts for manufacturing acetic acid at an industrially acceptable rate. The rates of acid formation using the chelating-phosphine iridium complexes are less than those achieved with monodentate ligand complexes, but this is understandable in view of the decreased bonding by the metal with carbon monoxide. However, the prior art catalysts are extremely volatile, compared to the chelated complexes, and must be replaced in the reactor. The chelating complexes are thermally more stable than the prior art complexes, and difficult to remove metal deposition is minimized.

The above results also indicate that addition of excess chelating ligand to reaction mixtures suppresses the rate of acetic acid production. Maximum rates, without sacrificing low volatility, are achieved with a phosphorus to iridium ratio of from 1–2:1. As the P/Ir ratio increases, the excess ligand competes with carbon monoxide for catalyst sites on the metal and retards the rate of acid production.

What is claimed is:

1. In a carbonylation process which comprises contacting a reactant selected from the group having the formula (a) ROH where R is a saturated hydrocarbyl radical having from about 1 to 20 carbon atoms, (b) $R_a-O-R_a$ or

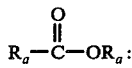

wherein $R_a$ is a saturated hydrocarbyl radical having from about 1 to 19 carbon atoms and wherein the total number of carbon atoms in formulas $R_a-O-R_a$ or

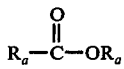

does not exceed about 20 and (c) R—X where R is a saturated hydrocarbyl radical of 1 to 20 carbon atoms and X is a halogen atom selected from the group consisting of bromine, chlorine and iodine, with carbon monoxide, in the presence of a catalyst consisting essentially of (1) an iridium compound and (2) a halogen component, the improvement which comprises employing as the iridium compound an iridium complex formed between an iridium compound and a phosphorus or arsenic ligand of the formula:

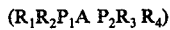

in which the molar ratio of chelating ligand to iridium is at least 1
wherein:
$R_1$ and $R_3$ are alkenyl groups having from 2 to 6 carbon atoms, alkyl groups having from 1 to 6 carbon atoms, hydrogen atoms, phenyl groups, and substituted phenyl, said substituents selected from the group consisting of nitro and fluorine groups;

$R_2$ and $R_4$ are phenyl groups and substituted phenyl groups, said substituents selected from the group consisting of nitro and fluorine groups;

$P_1$ and $P_2$ are phosphorus or arsenic;

A is a phenylene group, an alkenyl group having from 2 to 4 carbon atoms and $(CH_2)_n$ where $n$ is from 1–4; and carrying out said process at a temperature of from about 160° C to about 250° C.

2. The process of claim 1 wherein A in said formula is $(CH_2)_n$.

3. The process of claim 2 wherein said reaction is carried out in an aqueous acidic reaction medium.

4. The process of claim 2 wherein $R_1$ is phenyl or a substituted derivative thereof.

5. The process of claim 4 wherein $R_3$ is phenyl or a substituted derivative thereof.

6. The process of claim 5 wherein $R_2$ and $R_4$ are phenyl.

7. The process of claim 6 wherein $P_1$ and $P_2$ in said formula are phosphorus.

8. The process of claim 7 wherein $n$ is either 1 or 3 and the ratio of phosphorus in the ligand to iridium is from about 1–2:1.

9. The process of claim 8 wherein said reactant is an alcohol.

10. The process of claim 9 wherein said halogen component is an iodine providing component.

11. The process of claim 10 wherein said reactant alcohol is methanol.

12. The process of claim 11 wherein said process is carried out at a temperature of from about 190° C to about 210° C.

* * * * *